| United States Patent [19] | [11] Patent Number: 5,002,566 |
| --- | --- |
| Carpentier et al. | [45] Date of Patent: Mar. 26, 1991 |

[54] CALCIFICATION MITIGATION OF BIOPROSTHETIC IMPLANTS

[75] Inventors: Alain Carpentier; Sophie Carpentier, both of Paris, France; Aws Nashef, Huntington Beach, Calif.

[73] Assignee: Baxter International Inc., Deerfield, Ill.

[21] Appl. No.: 339,787

[22] Filed: Apr. 18, 1989

Related U.S. Application Data

[63] Continuation-in-part of Ser. No. 312,542, Feb. 17, 1989, abandoned.

[51] Int. Cl.$^5$ ................................................ A61F 2/24
[52] U.S. Cl. ........................................ 623/2; 623/11; 8/94.28; 8/94.19 R
[58] Field of Search ...................................... 623/1-3, 623/11, 12, 66; 427/2; 128/DIG. 8; 8/94.28, 94.19

[56] References Cited

U.S. PATENT DOCUMENTS

| | | |
| --- | --- | --- |
| 1,892,410 | 12/1932 | Rohm et al. . |
| 3,974,526 | 8/1976 | Dardik et al. . |
| 4,097,234 | 6/1978 | Sohde et al. . |
| 4,323,358 | 4/1982 | Lentz et al. . |
| 4,378,224 | 3/1983 | Nimni et al. . |
| 4,481,009 | 11/1984 | Nashef . |
| 4,553,974 | 11/1985 | Dewanjee . |
| 4,648,881 | 3/1987 | Carpentier et al. . |

*Primary Examiner*—Alan W. Cannon
*Attorney, Agent, or Firm*—Michael C. Schiffer

[57] ABSTRACT

Calcification resistant bioprosthetic implants are made from tanned biological materials, such as porcine heart valves, bovine pericardium, human dura mater or the like, which has been impregnated with a calcification-mitigating effective amount of a ferric and/or stannic salt. The impregnated biological materials and processes are particularly advantageous for the preparation of bioprosthetic heart valves. These implants have been found to be highly resistant to calcification in vivo.

18 Claims, No Drawings

CALCIFICATION MITIGATION OF BIOPROSTHETIC IMPLANTS

RELATED APPLICATIONS

This is a continuation-in-part of application originally filed under Ser. No. 312,542 on Feb. 17, 1989, now abandoned.

BACKGROUND OF THE INVENTION

This invention relates to calcification-resistant bioprosthetic implants and to a process for preparing them. More particularly, the invention concerns calcification-resistant bioprosthetic heart valves prepared from naturally derived biological materials.

Bioprosthetic heart valves, such as glutaraldehyde preserved porcine heart valves, have overcome numerous problems associated with mechanical and homograft heart valves. These bioprosthetic valves are quite stable and non-antigenic, have a remarkable durability and have physical characteristics which closely mimic the natural valves.

An alternative technique for the tanning or preservation of animal hides and tissues involves the use of metallic salts. Chrome tanning, for example, has been employed for many years in the leather industry. (See, e.g., U.S. Pat. No. 1,892,410.) Ferric, chromium and aluminum salts have been used for tanning naturally derived collagen, which may be used for preparing implantable prosthetic articles. (See U.S. Pat. No. 4,097,234.) Dardik, et al., in U.S. Pat. No. 3,974,526, describe the preparation of bioprosthetic vascular grafts from veins and arteries obtained from the umbilical cord. Among the reagents disclosed for hardening or tanning the vessels is chromium oxide.

A recurrent problem with such bioprosthetic heart valves has been their tendency toward calcification in vivo. This problem has been particularly prevalent in children, leading some to recommend against the use of bioprosthetic heart valves in children.

Various procedures for mitigating calcification of bioprosthetic heart valves have been proposed. For example, Lentz et al., in U.S. Pat. No. 4,323,358, disclose the treatment of implantable glutaraldehyde-fixed natural tissues (including porcine heart valves) with a soluble salt of a sulfated higher aliphatic alcohol to inhibit calcification after implantation. Nimni et al., in U.S. Pat. No. 4,378,224, disclose a procedure for inhibiting calcification of bioprosthetic tissues which involves cross-linking the tissue with a sulfated protein-polysaccharide, such as chondroitin sulfate. In U.S. Pat. No. 4,481,009, A. S. Nashef discloses a calcification mitigation procedure which comprises incorporating a biocompatible polymer into a bioprosthetic tissue prior to implantation tissue. Dewanjee et al., in U.S. Pat. No. 4,553,974, describe a multi-step procedure for treating biological tissues to inhibit calcification. This procedure involves treating the tissue with a surfactant, washing to remove the surfactant, fixing the tissue with glutaraldehyde, treating with a calcification inhibitor, such as an amino diphosphonate and treating the tissue with a reducing agent. U.S. Pat. No. 4,648,881, Carpentier et al., teaches that calcification of implanted biological tissue can be mitigated by avoiding contact of the tissues with phosphate-containing solutions, at least during the latter stages of their preparation. This patent also teaches that treatment of the tissue with a calcium-competitive divalent cation inhibits calcification of the implanted tissue.

A need continues to exist for a convenient, reliable and effective process for preparing calcification-resistant bioprosthetic implants, such as heart valves. Such a procedure should not deleteriously affect the durability, biocompatibility or physical characteristics of the bioprosthesis, and should be amendable to use in a commercial production process.

SUMMARY OF THE INVENTION

In accordance with the present invention, a calcification-resistant bioprosthetic implant comprises a tanned biological material, which is impregnated with a calcification-inhibiting amount of ferric or stannic ions or a mixture thereof. In one embodiment, the invention resides in a process for preparing a bioprosthetic implant, which comprises treating a biological tissue with a tanning agent to produce a biologically compatible, durable tissue, treating the biological tissue either before or after tanning, with an impregnation effective amount of a solution of a ferric or stannic salt, and forming the treated biological tissue into a prosthetic implant.

The bioprosthetic implants of this invention exhibit excellent resistance to calcification for long periods of implantation. The calcification mitigation process does not deleteriously affect the physical characteristics, the durability or biocompatibility of the implants.

DESCRIPTION OF THE PREFERRED EMBODIMENTS

Calcification is a particularly troublesome problem when it occurs in prosthetic heart valves. To function effectively, such heart valves must retain the high degree of flexibility and durability of the tissues from which they are made. The valves must not only be substantially non-antigenic, thus resistant to host rejection reactions, but they also must not be thrombogenic or stimulate inflammatory reactons. Such bioprosthetic valves should provide many years of trouble-free performance. If they do fail, their failure should be attended by a gradual decrease in performance, rather than by a catastrophic loss of function.

Calcification can compromise many of these desired characteristics. Calcification reduces the flexibility of the valvular materials, and can result in sudden, unpredictable failure of the valve. Mineral deposits on the valves may cause the formation of thrombi, which, if suddenly released can cause serious complications, including cerebrovascular or cardiovascular blockage. Calcification often requires premature replacement of bioprosthetic valves, thus exposing the patient to the risks of additional surgery.

It has now been discovered that by impregnating the biological materials used for making bioprosthetic heart valves with an effective amount of ferric or stannic ions or a mixture thereof, calcification can be substantially reduced.

The heart valves that may be prepared by this procedure include all of the common types of valves prepared from natural tissues, including those prepared from porcine heart valves, bovine pericardium, human dura matter and the like.

The process of the invention is generally employed in combination with any suitable process of sterilizing and fixing (tanning) the biological tissue. These tanning processes improve the durability and reduce the antigenicity of the biological tissue.

Any of the conventional tissue tanning or fixing procedures can be employed. A preferred procedure is to treat the tissue with 0.625% glutaraldehyde in either phosphate-buffered solutions or phosphate-free buffers. Phosphate-free buffers are preferred, and include, for example, borate, carbonate, bicarbonate, cacodylate, and other synthetic, artificial or organic buffers, such as N-2-Hydroxyethylpiperazine-N'-2-3thanesulphonic acid (HEPES), 2-(N-morpholino)propane-sulphonic acid (MOPS) and 1,4-piperazinebis(Ethanesulphonic acid) (PIPES).

Any of a variety of sterilizing procedures can be employed for sterilizing the bioprosthetic implants of this invention. A preferred procedure includes contacting the biological tissue with a sterilization-effective amount of a solution of formaldehyde or glutaraldehyde, an alcohol and a surfactant.

The sterilization and tanning procedures may be performed before or after the calcification mitigation procedure of the invention. The aldehydes used in the tanning process covalently cross-link with protein amine groups. Cross-linking of these groups, e.g., with glutaraldehyde, is important to reduce the antigenicity of the bioprosthesis. Ferric or stannic ions are believed to form stable, covalently bound complexes or ligands with amine groups, when in the presence of an aldehyde or other substance which will form Schiff bases with the amine groups.

Thus, the reaction of the ferric and/or stannic ions with the amine groups directly competes with the tanning process. Various methods have been devised to measure the extent to which the amine groups have become cross-linked. One method of determining the extent of the cross-linking of the amine groups is measuring of the temperature at which the biological tissue experiences shrinkage ($T_S$). Natural tissue typically has a $T_S$ of about 65° C. As the cross-linking increases the $T_S$ increases. Glutaraldehyde fixed tissue has a $T_S$ of about 84° C. to 85° C. This increase in hydrothermal stability of the tissue is believed to be important in terms of increased biological stability. Hence, it is desirable to insure that the impregnation with ferric and/or stannic ions does not significantly interfere with this $T_S$.

A high concentration of ferric or stannic salt may adversely affect the biological material. Such adverse effects range from a stiffening of the tissue to an actual increase in the tendency toward calcification. On the other hand, if the concentration of the ferric or stannic salt is too low, the treatment will not achieve the desired efficacy. The concentration of the ferric or stannic salt in solution may also affect the uniformity and depth of the penetration of the metallic ions throughout the biological material. In general, a uniform, deep penetration of the ferric or stannic ions in the biological material is preferred.

If the biological tissue is subjected first to the tanning solutions, then care must be taken to ensure that the biological tissue can be impregnated with a calcification mitigation amount of the ferric or stannic ions. Contrarily, if the biological tissue is first subjected to the treatment with the ferric or stannic ion solution, care must be taken to prevent the impregnation of such a large concentration of the ferric and/or stannic ions to prevent either adequate tanning, or to cause the biological material to become stiff.

As stated, there are many factors which influence the degree of impregnation. Firstly, the concentration of the ferric or stannic ions in the impregnation solution will influence the quantity of ions available for impregnation. The extent of impregnation is influenced by the amount of contact time between the impregnation solution and the biological material, the impregnation solution pH, and the sequence of performing the impregnation process and the tanning process. These factors are controlled to obtain the desired impregnation level of ferric or stannic ion in the tissue.

The precise level of ferric and/or stannic ion impregnation for a specific biological tissue is dependent upon the desired end use. As stated, the ferric and stannic ion impregnation competes with the cross-linking action of the aldehydes during the tanning process. This will directly affect the $T_S$, which is dependent upon the degree of cross-linking obtained during the tanning process. Tissue impregnation with the ferric and/or stannic ions may also effect other characteristics of the tissue, such as flexibility of the tissue. The importance of any one characteristic is dependent upon the desired end usage for the tissue.

Accordingly, the effective amount of ferric and/or stannic ion impregnation is dependent upon the desired end usage. Biological tissue materials used to form tissue heart valves are usually required to possess a certain degree of flexibility. As the level of ferric and/or stannic ion impregnation increases, the tissue loses flexibility. However, a sufficient amount of ferric and/or stannic ions must be incorporated to provide the necessary degree of calcification mitigation. As stated, the impregnation with ferric and/or stannic ions is highly dependent upon the concentration in the impregnating solution and the conditions under which the biological tissue material is subjected to the impregnation process.

As stated, one indicator used to measure the usefulness of biological material subjected to the tanning process is the measurement of the temperature of shrinkage ($T_S$). $T_S$ is measured by holding the tissue within two clamps. One of the clamps is mounted in a manner to allow the clamp to slide in direction generally parallel to the direction in which the tissue is being held. This clamp is coupled to a device capable to indicating movement of the clamp. The tissue is immersed in a bath. The temperature of the bath is slowly raised until observing movement of the clamp.

The process of the invention is performed in conjunction with a tanning process until the tissue is sufficiently impregnated with a calcification mitigating amount of ferric and/or stannic ions to achieve the desired calcification mitigation, while remaining sufficiently pliable for the intended end use. Once the desired degree of impregnation and pliability is obtained for a desired end use a measurement of the $T_S$ provides an adequate reference point for tissue stabilization.

For example, it has been determined that biological tissue tanned using glutaraldehyde should have a $T_S$ of from about 85° C. to possess the desired stability. Accordingly, the degree to which the tissue is impregnated with ferric and/or stannic ion should be maximized while maintaining this desired $T_S$.

The process of the invention is generally performed by contacting the biological material with a solution of a water-soluble ferric or stannic salt. This contact typically requires immersing the biological materials in the treatment solution. Alternatively, the solution may be sprayed, roll coated or applied to the biological materials using any suitable procedure. In a preferred embodiment, the biological material is immersed in the ferric or stannic salt solution for a period of time ranging from about 24 hours to about 200 hours.

The solvent or vehicle for the ferric or stannic salt may be an organic solvent system or an aqueous solvent. Examples of organic solvents which may be used include lower $C_1$-$C_8$ aliphatic alcohols, glycols, triols, aldehydes and the like.

Preferred solvent systems are aqueous solutions of water-miscible alcohols, glycols, triols and aldehydes. These aqueous solvent systems not only serve as a vehicle for the ferric or stannic salts, but also serve as protein denaturants and bacteriocidal agents. Examples of such solvent systems are aqueous solutions of ethanol, formaldehyde, glutaraldehyde, glycerol or mixtures thereof. These aqueous solvent systems have the added advantage that they have long been used in the treatment of implantable biological tissues, and their safety and effectiveness are well-established. The aqueous solvent systems advantageously contain up to about 30% ethanol, up to about 5% formaldehyde, up to about 0.625% glutaraldehyde, or up to about 30% glycerol, or mixtures thereof. These solvent systems can also advantageously contain conventional buffering agents.

The ferric or stannic ions are in the form of a soluble, substantially non-toxic salt. Examples of such salts include the nitrate, sulfate, borate, carbonate, halide, citrate and acetate salts. Preferred salts are ferric nitrate, stannic nitrate, ferric sulfate, stannic sulfate, ferric chloride, stannic chloride, ferric citrate, stannic citrate, ferric acetate and stannic acetate. Ferric salts are particularly preferred.

The ferric or stannic salt is employed in the solution in an impregnation effective concentration. Such concentration is an amount sufficient to impregnate the biological material with a calcification- mitigating amount of the ferric or stannic ions upon treatment with the solution. Generally, the concentration of the ferric or stannic salts in the solution which are applied to the tissue, will range from about 0.01% by weight to about 2.5% by weight, preferably from about 0.05% by weight to about 1.5% by weight. The ferric or stannic concentration in the tissue prior to implantation ranges from about 0.001% to about 3.0%, preferably from about 0.005% to about 1.0% by weight.

The pH of the ferric or stannic salt solution has been found to affect the rate at which the ferric and/or stannic ions are absorbed by the biological tissue. The lower the pH, the faster the absorption. The pH of the solution generally ranges from about 2 to about 7, with the pH preferably ranging from about 4.5 to about 6 being preferred.

While the invention is particularly advantageous for preparing bioprosthetic heart valves, the biological materials and processes of this invention may be applied to the preparation of other types of implants. Examples of such implants are materials for bladder reconstruction, repair of blood vessels, and orthopedic implants, to name but a few.

The invention is further illustrated by the following examples, which are not intended to be limiting.

The discovery that led to the present invention was made by accident. Porcine heart valve leaflets were treated with glycerol prior to implantation into experimental animals. The leaflets were removed after several weeks, and were observed to have significantly lower levels of calcification than expected from prior experience. In investigating the cause of this result, it was noted that the glycerol used for treating the heart valve leaflets was taken from a metal container. This container of glycerol was quite old, and the glycerol was later found to contain relatively large amounts of iron and tin. Analysis of the glycerol for metals revealed that it contained 10 parts per million ("ppm") calcium, 90 ppm iron and 30 ppm tin. Follow-up experiments suggested that the lower degree of calcification was attributable to the contaminated glycerol. A series of experiments was conducted to establish the effect of the "aged glycerol" on calcification mitigation and development of alternate solution that would achieve this effect.

EXAMPLES 1-5

Standard tanning and calcification mitigation procedures were followed in each of the Examples 1-5. Each example included two or more samples. Example 1 involved the use of the aged glycerol discussed above, and demonstrates that the aged glycerol provided a degree of calcification mitigation. The remaining examples established that the providers of this calcification mitigation were ferric and stannic ions.

The only differences in the procedures between Examples 2-5 is in the type and concentration of ferric compound used during the calcification procedure. The specific compound and concentration level is indicated for each sample of the various examples.

The standard procedures for the Examples 2-5 were as follows: Freshly extracted porcine aortic heart valve leaflets were thoroughly rinsed with isotonic saline solution. The leaflets were then subjected to tanning and calcification procedures, with the calcification mitigation procedure, unless otherwise indicated, being performed first. In one of the samples of Example 2 the procedures were reversed. This demonstrated that the calcification procedure would work whether performed before or after the tanning procedure.

The calcification procedure involved immersing the leaflets in one of two types of glycerol solutions. The first type of solution, designated as $aaa_B$ in the examples, is the aged glycerol solution discussed above, while the second type of solution, designated as $aaa_C$, is commercial grade glycerol solution consisted of ⅓ ethanol (90%), ⅓ aqueous formaldehyde (prepared by mixing 4 parts 37% formaldehyde and 6 parts $H_2O$) and ⅓ glycerol. The $aaa_C$ glycerol solution was either used alone or spiked with a ferric or stannic compound. This is designated in the several examples by an indication along with the designation $aaa_C$ of a percent concentration, as a weight/volume percent, of the selected ferric or stannic compound. The ferric or stannic compounds used were either salts or oxides.

The tanning procedure (indicated in the various examples by "Glut Mg") involved immersing the leaflets in a solution consisted of 0.625 percent, on a weight/volume basis, glutaraldehyde having a pH of 7.4±0.1 containing 0.02 molar N-2-Hydroxyethylpiperazine-$N^1$-2-Ethane-sulfonic acid (HEPES), 0.26 weight/volume percent magnesium chloride and a sufficient amount of sodium chloride to prepare an isotonic solution.

Both the tanning and calcification procedures were performed by immersing the leaflets in the respective solutions for a one week period.

After the tanning and calcification procedures were completed the leaflets were surgically implanted subcutaneously at various locations into the backs of growing rats (Examples 2-5) or growing rabbits (Example 6). These leaflets were left implanted for those periods of time indicated for each example. Three leaflets were implanted in each rat used for the examples 1-5, with two rats being sacrificed for each time interval. After the rats were sacrificed the leaflets were removed and observed for calcification. The calcification was measured qualitatively in Examples 2-5. The qualitative procedure used for Examples 2-5 involved visual inspection and recording of the extent of calcification using a calcification scale of: no observable calcification (0), some calcification (+), average amount of the calcification (++) or severe calcification (+++). A letter F indicates minute degree of calcification observed under microscope. A letter E indicates that calcification was in the cells only, and represents only minor calcification. Generally, the samples being observed at each time interval possessed different degrees of calcification. As seen in the following charts, two different indications are given for each sample. This represents different degrees of calcification between the six different leaflets. However, except for certain examples, marked accordingly, no attempt was made to record the precise number of leaflets having each type of calcification. In Example 3 the respective number of leaflets for each grade is provided, while in Examples 2 and 5, two grade is provided for the leaflets. The grading was performed by visual observation. First, an X-ray of each sample was observed to provide a general indication of calcification. If a greater degree of differentiation was needed then a leaflet section was stained and examined for calcification. The stained section was prepared by embedding the leaflets in a paraffin block, sectioning the blocks and staining the sections with Von Kossa stain.

EXAMPLE 1

This example illustrates the benefit provided by the aged glycerol described above. Treatment 1 included the immersing of the leaflets in the aged glycerol without the tanning procedure, while treatment 2 is merely leaflets subjected to the tanning procedure alone.

| TREATMENT No. | 1 MONTH | 2 MONTHS | 3 MONTHS | 4 MONTHS |
|---|---|---|---|---|
| (1) $aaa_B$ | 6 (0) | 4 (0) 2 (lost) | — | 1 (0) 2(+++) |
| (2) Glut-P | ++ | +++ | — | 3 (lost) |

The number of leaflets observed is indicated for the treatments. This example demonstrates the calcification mitigation effect of the $aaa_B$, but that without tanning the resulting tissue is unstable. The indication of "lost" means that the tissue was digested and absorbed by the animal.

EXAMPLE 2

This example demonstrates that, the anti-calcification treatment when coupled with tanning of the tissue, provides for a biologically stable tissue having a good degree of calcification mitigation. Treatment 1 was not subjected to tanning.

| TREATMENT NO. | 2 MONTHS | 3 MONTHS | 4 MONTHS |
|---|---|---|---|
| (1) $aaa_B$ | 0/+++ | 0/+++ | 0/+++ |
| (2) Glut Mg/$aaa_B$ | 0/E | 0/E | 0/+++ |
| (3) $aaa_B$/Glut Mg | 0 | 0 | 0 |

EXAMPLE 3

This example demonstrates that commercial glycerol $aaa_C$ does not provide the calcification mitigation as does $aaa_B$.

| TREATMENT NO. | 4 MONTHS | 6 MONTHS | 8 MONTHS | 11 MONTHS |
|---|---|---|---|---|
| (1) $aaa_B$/Glut Mg | 9(0) 3(F) | 6(0) 3(F) | 6(0) 5(F) | 1(0) |
| (2) $aaa_C$/Glut Mg | 4(0) 2(++) | 4(0) 2(++) | | |

In this example three rats were sacrificed for the first three time intervals for treatment (1).

This example demonstrates that the calcification mitigation is provided by the ferric ions as ferric salts. The use of ferric oxide (treatment 5) did not provide for calcification mitigation.

| TREATMENT NO. | 2 MONTHS | 4 MONTHS | 6 MONTHS |
|---|---|---|---|
| (1) $aaa_B$/Glut Mg | 0 | 0 | |
| (2) $aaa_C$/Glut Mg | +++ | | |
| (3) $aaa_C$/Glut Mg + $FeCl_3$(50 mg/ 100 ml $aaa_C$) | 0 | 0 | |
| (4) $aa_C$/Glut Mg + $Fe_2(SO_4)_3 \cdot nH_2O$:2.6% w/v | F | F | + |
| (5) $aaa_C$/Glut Mg + $Fe_2O_3, 2H_2O$(50 mg/ 100 ml $aaa_C$) | +++ | | |
| (6) $aaa_C$/Glut Mg + $Fe(NO_3)_3, 3H_2O$: 2.6% w/v | 0 | 0 | 0 |

EXAMPLE 5

This example demonstrates the usefulness of both ferric and stannic salts (ions) in providing the calcification mitigation.

| TREATMENT NO. | 4 MONTHS | 6 MONTHS | 8 MONTHS | 10 MONTHS |
|---|---|---|---|---|
| (1) $aaa_B$/Glut Mg | 0 | 0/F | F/++ | 0/++ |
| (2) $aaa_C$/Glut Mg | + | + | ++ | +++ |
| (3) $aaa_C$/Glut Mg + $FeCl_3$: 3.3% w/v | 0 | 0/F | F | 0/+++ |
| (4) $aaa_C$/Glut Mg + $SnCl_5$: 6% w/v | + | F | 0/++ | 0/+++ |
| (5) $aaa_C$/Glut Mg + ,$2H_2O$: 2% w/v | +++ | | | |
| (6) $aaa_C$ + $CaCl_2$ 2% w/v + $SnCl_5$ 6% w/v + $FeCl_3$ 3.3% w/v | +++ | | | |

The last two samples 5 and 6 indicate that presence of calcium ions negates the calcification mitigation effect of stannic and ferric ions.

EXAMPLE 6

6 quantitatively measured the concentration of both calcium (Ca) and Iron (Fe) in the implanted leaflets. The calcification and tanning procedures used to prepare the leaflets for the samples of this example were as performed above. The treatment codes listed for the samples indicate two types of treatment. Treatment E is with the aged glycerol aaa$_B$ followed by the tanning procedure discussed above. Treatment F uses commercial grade glycerol spiked with 0.1 weight/volume percent ferric nitrate followed by the tanning procedure discussed above. The complete procedure for this example involved taking a saline stored leaflet, subjecting the leaflets to the calcification procedure described above, using the indicated solutions, for one week, followed by the described tanning procedure with glutaraldehyde for one week. The leaflets were then sterilized in a FETH (4% Formaldehyde-22.5% ethanol-1.2% Tween (a polysorbate 80 anionic surfactant −0.02 Molar HEPES with the solution having a pH of 7.4) for nine hours at 35° C.

The procedure used for implanting and observing calcification of the leaflets in Example 6 were also different than those described above. First, the leaflets were implanted subcutaneously in the backs of six growing rabbits. Secondly, twelve leaflets were implanted in each rabbit six on each side of the spine. For each time interval, three leaflets were removed and the quantitative measurement was performed on each leaflet. The quantitative measurement of Ca and Fe used in Example 6 is as follows: At each indicated time interval the leaflets were explanted and rinsed with saline to remove the blood. X-rays of the leaflets were made to allow for visual observation. The tissue growth about the leaflets was then removed by suitable mechanical means. The cleaned leaflets were then subjected to a lyophilisation procedure until dried. This typically requiring sixteen hours. The dry weight for each leaflet was recorded, and then the leaflets were digested in 3 Normal nitric acid, with the remaining volume adjusted to 10 millimeters of distilled H$_2$O in a volumetric flask. The percentage of calcification, or calcium content, and also iron content, was determined using elemental analysis by atomic absorption for each leaflet. The percentage of calcium and iron as indicated in Table 1 below is the average for the three leaflets from each rabbit.

The percentage of calcium and iron in the tissue of treatment E before implantation was measured to be 0.012 for calcium and 1.295 for iron and for treatment F, 0.005 for calcium and 1.662 for Fe. As can be seen the amount of calcium uptake was minimal over the twelve week period.

TABLE 1

| Sample Number | Treatment Code | Implant time (weeks) | | | | | | | |
|---|---|---|---|---|---|---|---|---|---|
| | | 3 | | 6 | | 9 | | 12 | |
| | | Ca | Fe | Ca | Fe | Ca | Fe | Ca | Fe |
| 1 | E | 0.183 | 2.293 | 0.065 | 0.411 | 0.117 | 0.560 | 0.098 | 0.901 |
|   | F | 0.088 | 0.935 | 0.004 | 0.842 | 0.151 | 1.090 | 0.071 | 0.933 |
| 2 | E | 0.124 | 0.490 | 0.022 | 0.503 | 0.222 | 0.731 | 0.100 | 0.788 |
|   | F | 0.060 | 0.842 | 0.031 | 1.022 | 0.077 | 1.001 | 0.118 | 0.799 |
| 3 | E | 0.173 | 0.630 | 0.033 | 0.705 | 0.173 | 0.666 | 0.077 | 0.663 |
|   | F | 0.068 | 0.875 | 0.037 | 0.865 | 0.067 | 0.916 | 0.083 | 1.196 |
| 4 | E | 0.082 | 0.520 | 0.033 | 0.632 | 0.137 | 0.561 | 0.034 | 0.406 |
|   | F | 0.071 | 0.745 | 0.021 | 0.942 | 0.103 | 0.948 | 0.053 | 1.009 |
| 5 | E | 0.110 | 0.795 | — | — | 0.143 | 0.786 | 0.073 | 0.723 |
|   | F | 0.105 | 0.775 | 0.011 | 1.042 | — | — | 0.269 | 1.022 |
| 6 | E | 0.106 | 0.747 | 0.008 | 0.450 | 0.172 | 0.332 | 0.117 | 0.680 |
|   | F | 0.111 | 0.909 | 0.012 | 0.924 | 0.079 | 0.986 | 0.083 | 1.221 |

While the preferred embodiments have been described, various modifications and substitutions may be made thereto without departing from the scope of the invention. Accordingly, it is to be understood that the invention has been described by way of illustration and not limitation.

What is claimed is:

1. A process for making a calcification-resistant biological material comprising applying to said material a solution comprising an ion selected from the group consisting of ferric ions, stannic ions, or a combination of ferric and stannic ions to impregnate said material with a calcification-mitigating effective amount of said ferric ions, stannic ions, or a combination of ferric and stannic ions, wherein the biological material is tanned prior to said step of applying said solution.

2. The process of claim 1 wherein the biological material is tanned subsequent to said step of applying said solution of ferric and/or stannic salt.

3. The process of claim 1 wherein the biological material is impregnated with ferric ion.

4. The process of claim 1 wherein the biological material is impregnated with stannic ion.

5. The process of claim 1 wherein the biological material is impregnated with a mixture of ferric and stannic ions.

6. The process of claim 1, which further comprises forming the bioprosthesis into a heart valve.

7. The process of claim 1 which further comprises sterilizing the bioprosthesis.

8. The process of claim 1 wherein the biological material is impregnated with the ferric or stannic ions by treatment with a solution of a soluble, substantially non-toxic ferric or stannic salt.

9. The process of claim 8 wherein the salt is a nitrate, sulfate, borate, carbonate, halide, citrate or acetate of ferric or stannic.

10. The process of claim 9 wherein the salt is dissolved in an aqueous solution of water-miscible alcohol, glycol, triol, or aldehyde.

11. The process of claim 9 wherein the salt is dissolved in an aqueous solution of ethanol, formaldehyde, glutaraldehyde, or glycerol.

12. The process of claim 11 wherein the pH of the solution ranges from about 2 to about 7.

13. The process of claim 11 wherein the pH of the solution ranges from about 2 to about 3.

14. The process of claim 11 wherein the solution contains from about 0.01% to about 2.5% by weight of the ferric or stannic salt.

15. The process of claim 14, wherein the solution contains from about 0.05% to about 1.5% of the ferric or stannic salt.

16. The process of claim 9 wherein the solution contains up to about 30% ethanol, up to about 5% formaldehyde, up to about 1% glutaraldehyde, or up to about 30% glycerol, or mixtures thereof.

17. The process of claim 8 wherein the salt is ferric nitrate, stannic nitrate, ferric sulfate, stannic sulfate, ferric chloride, stannic chloride, ferric citrate, stannic citrate, ferric acetate or stannic acetate.

18. A process for making a calcification-resistant biological material comprising applying to said material a solution comprising an ion selected from the group consisting of ferric ions, stannic ions, or a combination of ferric and stannic ions to impregnate said material with a calcification-mitigating effective amount of said ferric ions, stannic ions, or a combination of ferric and stannic ions, and wherein the solution contains up to about 30% ethanol, up to about 5% formaldehyde, up to about 1% glutaraldehyde, or up to about 30% glycerol, or mixtures thereof.

* * * * *